United States Patent
Kimura et al.

(10) Patent No.: US 7,217,839 B2
(45) Date of Patent: May 15, 2007

(54) METHOD OF PRODUCING NEAR-INFRARED ABSORBING DYE COMPOUND

(75) Inventors: Keizo Kimura, Odawara (JP); Tomohito Masaki, Odawara (JP); Katsuyoshi Yamakawa, Odawara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/515,911

(22) Filed: Sep. 6, 2006

(65) Prior Publication Data

US 2007/0055071 A1   Mar. 8, 2007

(30) Foreign Application Priority Data

Sep. 7, 2005   (JP)   ............................. 2005-259243

(51) Int. Cl.
*C07C 249/00* (2006.01)

(52) U.S. Cl. ..................................... 564/272

(58) Field of Classification Search ................ 564/272
See application file for complete search history.

(56) References Cited

U.S. PATENT DOCUMENTS 3,962,290 A   6/1976   Grosso

FOREIGN PATENT DOCUMENTS

| JP | 61-246391 A | 11/1986 |
|---|---|---|
| JP | 5-98243 A | 4/1993 |
| JP | 11-315054 A | 11/1999 |
| JP | 2003-55643 A | 2/2003 |

OTHER PUBLICATIONS

Zhifei Dai et al.; Journal of Dispersion Science and Technology; vol. 23, No. 4, pp. 555-562, 2002.

*Primary Examiner*—Samuel Barts
(74) *Attorney, Agent, or Firm*—Birch, Stewart, Kolasch & Birch, LLP

(57) ABSTRACT

A method of producing a near-infrared absorbing dye compound, useful for image forming materials, infrared heat-sensitive recording devices, optical film materials, and the like, containing a process of reacting a compound represented by formula (I) with halogenating agent.

Formula (I)

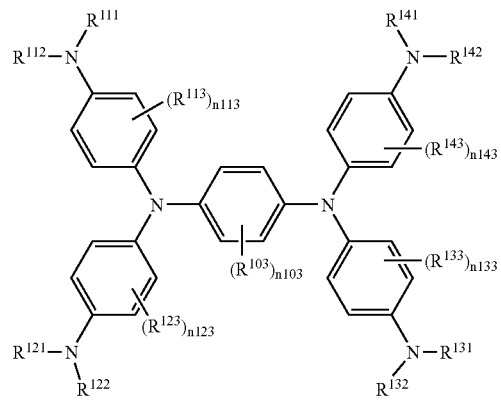

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

7 Claims, No Drawings

METHOD OF PRODUCING NEAR-INFRARED ABSORBING DYE COMPOUND

FIELD OF THE INVENTION

The present invention relates to a near-infrared absorbing dye compound useful for image forming materials, infrared heat-sensitive recording materials, optical recording devices, optical film materials, and the like. The present invention relates particularly to a method in which an aminium salt and a diimmonium salt that are near-infrared absorption dye compounds, can be produced readily at low costs, and in high yield.

BACKGROUND OF THE INVENTION

An aminium salt and a diimmonium salt are useful as near-infrared absorbing dyes that do not substantially absorb visible light but absorb infrared rays, and they have been studied enthusiastically (for example, JP-A-2003-280247 ("JP-A" means unexamined published Japanese patent application), JP-A-2003-295496, and JP-A-2004-145036).

As a method of producing an aminium salt or a diimmonium salt, methods in which an amino compound, that is a precursor, is oxidized by $Cu^{2+}$ (for example, JP-B-59-40825 ("JP-B" means examined Japanese patent publication) and JP-A-63-51462); by $Fe^{3+}$ (for example, JP-A-2-311447 and JP-A-11-315054); by utilizing an oxidizing reaction using a solid catalyst (for example, JP-A-5-98243); by a peroxodisulfate (for example, JP-A-2003-55643); by using silver hexafluoroantimonate (for example, Journal of Dispersion Science and Technology, vol. 23, p 555 (2002)), or by electrical oxidation (for example, JP-A-61-246391), have been known so far. All of these methods are unsatisfactory in yield, and they have also a large environmental load because of the use of heavy metal ions. These methods also have such problems as high costs.

SUMMARY OF THE INVENTION

The present invention resides in a method of producing a near-infrared absorbing dye compound, comprising a process of reacting a compound represented by formula (I) with halogenating agent:

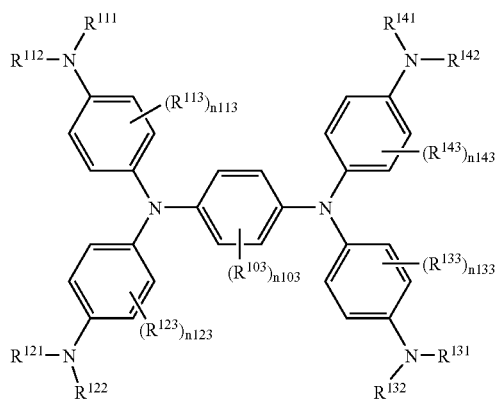

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

Other and further features and advantages of the invention will appear more fully from the following description.

DETAILED DESCRIPTION OF THE INVENTION

According to the present invention, there is provided the following means:

(1) A method of producing a near-infrared absorbing dye compound, comprising a process of reacting a compound represented by formula (I) with a halogenating agent:

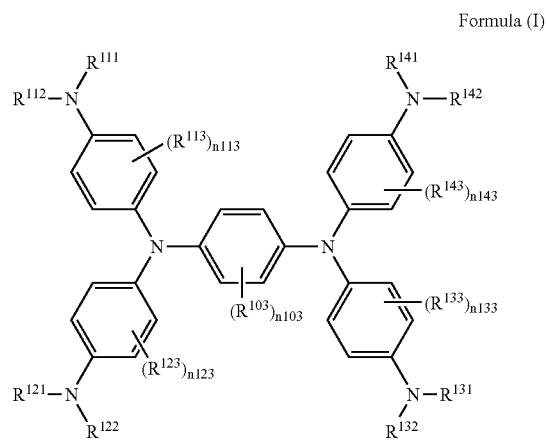

Formula (I)

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

(2) The production method according to the above item (1), wherein the halogenating agent is an organic halogenating agent.

(3) The production method according to the above item (1) or (2), wherein the halogenating agent is a chlorinating agent.

(4) The production method according to any one of the above items (1) to (3), wherein the halogenating agent is 1,3-dichloro-5,5-dimethylehydantoin.

(5) The production method according to any one of the above items (1) to (4), wherein the near-infrared absorbing dye compound is a diimmonium salt represented by formula (II):

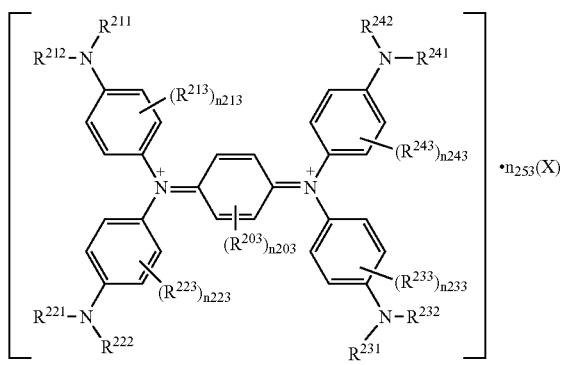

Formula (II)

wherein $R^{211}$, $R^{212}$, $R^{221}$, $R^{222}$, $R^{231}$, $R^{232}$, $R^{241}$ and $R^{242}$ each independently represent a hydrogen atom, an aliphatic group or an aromatic group; $R^{203}$, $R^{213}$, $R^{223}$, $R^{233}$ and $R^{243}$ each independently represent a substituent; $n_{203}$, $n_{213}$, $n_{223}$, $n_{233}$ and $n_{243}$ each independently denote an integer from 0 to 4; X represents a monovalent or divalent anion; and $n_{253}$ represents a number of 1 or 2, provided that the product of the valence number of X and $n_{253}$ is 2;

(6) The production method according to any one of the above items (1) to (5), wherein an acid or its salt coexists in the above process.

(7) The production method according to the above item (6), wherein the above acid or salt is perchloric acid or perchlorate.

Embodiments of the present invention will be explained hereinbelow.

In this specification, first, the aliphatic group means alkyl groups, substituted alkyl groups, alkenyl groups, substituted alkenyl groups, alkinyl groups, substituted alkinyl groups, aralkyl groups and substituted aralkyl groups. The alkyl groups may be branched or may form a ring (specifically, a cycloalkyl group). The number of carbon atoms of the alkyl group is preferably 1 to 20 and more preferably 1 to 18. The alkyl part of the substituted alkyl group is the same as the above alkyl group. The alkenyl part of the substituted alkenyl group is the same as the above alkenyl group. The alkenyl group may be branched or may form a ring (specifically, a cycloalkenyl group). The number of carbon atoms of the alkenyl group is preferably 2 to 20 and more preferably 2 to 18. The alkenyl part of the substituted alkenyl group is the same as the above alkenyl group. The alkinyl group may be branched or may form a ring (specifically, a cycloalkinyl group). The number of carbon atoms of the alkinyl group is preferably 2 to 20 and more preferably 2 to 18. The alkinyl part of the substituted alkinyl group is the same as the above alkinyl group. The alkyl group of the aralkyl group and substituted aralkyl group is the same as the above alkyl group. The aryl part of the aralkyl group and the substituted aralkyl group is the same as the following aryl group.

Examples of the substituent in the alkyl portion of the substituted alkyl group, substituted alkenyl groups, substituted alkinyl groups and substituted aralkyl groups include a halogen atom (e.g., fluorine, chlorine, bromine, iodine), an alkyl group [which means a linear, branched or cyclic substituted or unsubstituted alkyl group and which includes an alkyl group (preferably an alkyl group having from 1 to 30 carbon atoms, e.g., methyl, ethyl, n-propyl, isopropyl, tert-butyl, n-octyl, eicosyl, 2-chloroethyl, 2-cyanoethyl, 2-ethylhexyl), a cycloalkyl group (preferably a substituted or unsubstituted cycloalkyl group having from 3 to 30 carbon atoms, e.g., cyclohexyl, cyclopentyl, 4-n-dodecyl-cyclohexyl), a bicycloalkyl group (preferably a substituted or unsubstituted bicycloalkyl group having from 5 to 30 carbon atoms, namely, a monovalent group resultant from removing one hydrogen atom of a bicycloalkane having from 5 to 30 carbon atoms, e.g., bicyclo[1,2,2]heptan-2-yl, bicyclo[2,2,2]octan-3-yl), and a tricyclo-structure having many cyclic structures; the alkyl group in the substituents described below (for example, an alkyl group in an alkylthio group) means an alkyl group having such a concept and further includes an alkenyl group and an alkynyl group], an alkenyl group [which means a linear, branched or cyclic substituted or unsubstituted alkenyl group and which includes an alkenyl group (preferably a substituted or unsubstituted alkenyl group having from 2 to 30 carbon atoms, e.g., vinyl, allyl, prenyl, geranyl, oreyl), a cycloalkenyl group (preferably a substituted or unsubstituted cycloalkenyl group having from 3 to 30 carbon atoms, namely, a monovalent group resultant from removing one hydrogen atom of a cycloalkene having from 3 to 30 carbon atoms, e.g., 2-cyclopenten-1-yl, 2-cyclohexen-1-yl), and a bicycloalkenyl group (a substituted or unsubstituted bicycloalkenyl group, preferably a substituted or unsubstituted bicycloalkenyl group having from 5 to 30 carbon atoms, namely, a monovalent group resultant from removing one hydrogen atom of a bicycloalkene having one double bond, e.g., bicyclo[2,2,1]hept-2-en-1-yl, bicyclo[2,2,2]oct-2-en-4-yl)], an alkynyl group (preferably a substituted or unsubstituted alkynyl group having from 2 to 30 carbon atoms, e.g., ethynyl, propargyl, trimethylsilylethynyl), an aryl group (preferably a substituted or unsubstituted aryl group having from 6 to 30 carbon atoms, e.g., phenyl, p-tolyl, naphthyl, m-chlorophenyl, o-hexadecanoylaminophenyl), a heterocyclic group (preferably a monovalent group resultant from removing one hydrogen atom of a 5- or 6-membered substituted or unsubstituted aromatic or non-aromatic heterocyclic compound, more preferably a 5- or 6-membered aromatic heterocyclic group having from 3 to 30 carbon atoms, e.g., 2-furyl, 2-thienyl, 2-pyrimidinyl, 2-benzothiazoly), a cyano group, a hydroxyl group, a nitro group, a carboxyl group, an alkoxy group (preferably a substituted or unsubstituted alkoxy group having from 1 to 30 carbon atoms, e.g., methoxy, ethoxy, isopropoxy, tert-butoxy, n-octyloxy, 2-methoxyethoxy), an aryloxy group (preferably a substituted or unsubstituted aryloxy group having from 6 to 30 carbon atoms, e.g., phenoxy, 2-methylphenoxy, 4-tert-butylphenoxy, 3-nitrophenoxy, 2-tetradecanoylaminophenoxy), a silyloxy group (preferably a silyloxy group having from 3 to 20 carbon atoms, e.g., trimethylsilyloxy, tert-butyldimethylsilyloxy), a heterocyclic oxy group (preferably a substituted or unsubstituted heterocyclic oxy group having from 2 to 30 carbon atoms, e.g., 1-phenyltetrazol-5-oxy, 2-tetrahydropyranyloxy), an acyloxy group (preferably a formyloxy group, a substituted or unsubstituted alkylcarbonyloxy group having from 2 to 30 carbon atoms or a substituted or unsubstituted arylcarbonyloxy group having from 6 to 30 carbon atoms, e.g., formyloxy, acetyloxy, pivaloyloxy, stearoyloxy, benzoyloxy, p-methoxyphenylcarbonyloxy), a carbamoyloxy group (preferably a substituted or unsubstituted carbamoyloxy group having from 1 to 30 carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyloxy), an alkoxycarbonyloxy group (preferably a substituted or unsubstituted alkoxycarbonyloxy group having from 2 to 30 carbon atoms, e.g., methoxycarbonyloxy, ethoxycarbonyloxy, tert-butoxycarbonyloxy, n-octylcarbonyloxy), an aryloxycarbonyloxy group (preferably a substituted or unsubstituted aryloxycarbonyloxy group having from 7 to 30 carbon atoms, e.g., phenoxycarbonyloxy, p-methoxyphenoxycarbonyloxy, p-n-hexadecyloxyphenoxycarbonyloxy), an amino group (preferably an amino group, a substituted or unsubstituted alkylamino group having from 1 to 30 carbon atoms or a substituted or unsubstituted anilino group having from 6 to 30 carbon atoms, e.g., amino, methylamino, dimethylamino, anilino, N-methyl-anilino, diphenylamino), an acylamino group (preferably a formylamino group, a substituted or unsubstituted alkylcarbonylamino group having from 1 to 30 carbon atoms or a substituted or unsubstituted arylcarbonylamino group having from 6 to 30 carbon atoms, e.g., formylamino, acetylamino, pivaloylamino, lauroylamino, benzoylamino, 3,4,5-tri-n-octyloxyphenylcarbonylamino), an aminocarbonylamino group (preferably a substituted or unsubstituted aminocarbonylamino group having from 1 to 30 carbon atoms, e.g., carbamoylamino, N,N-dimethylaminocarbonylamino, N,N-diethylaminocarbonylamino, morpholinocarbonylamino), an alkoxycarbonylamino group (preferably a substituted or unsubstituted alkoxycarbonylamino group having from 2 to 30 carbon atoms, e.g., methoxycarbonylamino, ethoxycarbonylamino, tert-butoxycarbonylamino, n-octadecyloxycarbonylamino, N-methylmethoxycarbonylamino), an aryloxycarbonylamino group (preferably a substituted or unsubstituted aryloxycarbonylamino group having from 7 to 30 carbon atoms, e.g., phenoxycarbonylamino, p-chlorophenoxycarbonylamino, m-(n-octyloxy)phenoxycarbonylamino), a sulfamoylamino group (preferably a substituted or unsubstituted sulfamoylamino group having from 0 to 30 carbon atoms, e.g., sulfamoylamino, N,N-dimethylaminosulfonylamino, N-n-octylaminosulfonylamino), an alkyl- or aryl-sulfonylamino group (preferably a substituted or unsubstituted alkylsulfonylamino group having from 1 to 30 carbon atoms or a substituted or unsubstituted arylsulfonylamino group having from 6 to 30 carbon atoms, e.g., methylsulfonylamino, butylsulfonylamino, phenylsulfonylamino, 2,3,5-trichlorophenylsulfonylamino, p-methylphenylsulfonylamino), a mercapto group, an alkylthio group (preferably a substituted or unsubstituted alkylthio group having from 1 to 30 carbon atoms, e.g., methylthio, ethylthio, n-hexadecylthio), an arylthio group (preferably a substituted or unsubstituted arylthio group having from 6 to 30 carbon atoms, e.g., phenylthio, p-chlorophenylthio, m-methoxyphenylthio), a heterocyclic thio group (preferably a substituted or unsubstituted heterocyclic thio group having from 2 to 30 carbon atoms, e.g., 2-benzothiazolylthio, 1-phenyltetrazol-5-ylthio), a sulfamoyl group (preferably a substituted or unsubstituted sulfamoyl group having from 0 to 30 carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl), a sulfo group, an alkyl- or aryl-sulfinyl group (preferably a substituted or unsubstituted alkylsulfinyl group having from 1 to 30 carbon atoms or a substituted or unsubstituted arylsulfinyl group having from 6 to 30 carbon atoms, e.g., methylsulfinyl, ethylsulfinyl, phenylsulfinyl, p-methylphenylsulfinyl), an alkyl- or aryl-sulfonyl group (preferably a substituted or unsubstituted alkylsulfonyl group having from 1 to 30 carbon atoms or a substituted or unsubstituted arylsulfonyl group having from 6 to 30 carbon atoms, e.g., methylsulfonyl, ethylsulfonyl, phenylsulfonyl, p-methylphenylsulfonyl), an acyl group (preferably a formyl group, a substituted or unsubstituted alkylcarbonyl group having from 2 to 30 carbon atoms, a substituted or unsubstituted arylcarbonyl group having from 7 to 30 carbon atoms or a substituted or unsubstituted heterocyclic carbonyl group having from 4 to 30 carbon atoms and being bonded to a carbonyl group through a carbon atom, e.g., acetyl, pivaloyl, 2-chloroacetyl, stearoyl, benzoyl, p-n-octyloxyphenylcarbonyl, 2-pyridylcarbonyl, 2-furylcarbonyl), an aryloxycarbonyl group (preferably a substituted or unsubstituted aryloxycarbonyl group having from 7 to 30 carbon atoms, e.g., phenoxycarbonyl, o-chlorophenoxycarbonyl, m-nitrophenoxycarbonyl, p-tert-butylphenoxycarbonyl), an alkoxycarbonyl group (preferably a substituted or unsubstituted alkoxycarbonyl group having from 2 to 30 carbon atoms, e.g., methoxycarbonyl, ethoxycarbonyl, tert-butoxycarbonyl, n-octadecyloxycarbonyl), a carbamoyl group (preferably a substituted or unsubstituted carbamoyl group having from 1 to 30 carbon atoms, e.g., carbamoyl, N-methylcarbamoyl, N,N-dimethylcarbamoyl, N,N-di-n-octylcarbamoyl, N-(methylsulfonyl)-carbamoyl), an aryl- or heterocyclic-azo group (preferably a substituted or unsubstituted arylazo group having from 6 to 30 carbon atoms or a substituted or unsubstituted heterocyclic-azo group having from 3 to 30 carbon atoms, e.g., phenylazo, p-chlorophenylazo, 5-ethylthio-1,3,4-thiadiazol-2-ylazo), an imido group (preferably N-succinimido, N-phthalimido), a phosphino group (preferably a substituted or unsubstituted phosphino group having from 2 to 30 carbon atoms, e.g., dimethylphosphino, diphenylphosphino, methylphenoxyphosphino), a phosphinyl group (preferably a substituted or unsubstituted phosphinyl group having from 2 to 30 carbon atoms, e.g., phosphinyl, dioctyloxyphosphinyl, diethoxyphosphinyl), a phosphinyloxy group (preferably a substituted or unsubstituted phosphinyloxy group having from 2 to 30 carbon atoms, e.g., diphenoxyphosphinyloxy, dioctyloxyphosphinyloxy), a phosphinylamino group (preferably a substituted or unsubstituted phosphinylamino group having from 2 to 30 carbon atoms, e.g., dimethoxyphosphinylamino, dimethylaminophosphinylamino), or a silyl group (preferably a substituted or unsubstituted silyl group having from 3 to 30 carbon atoms, e.g., trimethylsilyl, tert-butyidimethylsilyl, phenyldimethylsilyl).

Among the above functional groups, those having a hydrogen atom may be further substituted with the above group at the position from which the hydrogen atom is removed. Examples of such a functional group include an alkylcarbonylaminosulfonyl group, arylcarbonylaminosulfonyl group, alkylsulfonylaminocarbonyl group and arylsulfonylaminocarbonyl group. Specific examples of these groups include methylsulfonylaminocarbonyl, p-methylphenylsulfonylaminocarbonyl, acetylaminosulfonyl and benzoylaminosulfonyl.

Examples of the substituent of the aryl part of the substituted aralkyl group include substituents of the following substituted aryl group.

The aromatic group in this specification means an aryl group and a substituted aryl group. Also, these aromatic groups may be condensed with aliphatic rings, other aromatic rings or hetero rings. The number of carbon atoms of the aromatic group is preferably 6 to 40, more preferably 6 to 30 and still more preferably 6 to 20. Among these groups, the aryl group is preferably phenyl or naphthyl and particularly preferably phenyl.

The aryl part of the substituted aryl group is the same as the above aryl group. Examples of the substituent of the substituted aryl group include those given as the substituents of the alkyl parts of the previous substituted alkyl group, substituted alkenyl group, substituted alkinyl group and substituted aralkyl group.

Next, the compounds represented by the formulae (I) and (11) will be explained.

In the formula (I), $R^{111}$, $R^{112}$, $R^{121}$, $R^{122}$, $R^{131}$, $R^{132}$, $R^{141}$ and $R^{142}$ are respectively preferably a hydrogen atom, an alkyl group, an alkenyl group, an alkinyl group or an aryl group, more preferably a hydrogen atom, an alkyl group having 1 to 20 carbon atoms, an alkenyl group having 2 to 20 carbon atoms, an alkinyl group having 2 to 20 carbon atoms or an aryl group having 6 to 20 carbon atoms, still more preferably an alkyl group having 1 to 10 carbon atoms, an alkenyl group having 2 to 10 carbon atoms or an aryl group having 6 to 10 carbon atoms, even more preferably an alkyl group having 1 to 8 carbon atoms or an aryl group having 6 to 8 carbon atoms and most preferably an alkyl group having 2 to 6 carbon atoms. Also, all of $R^{111}$, $R^{112}$, $R^{121}$, $R^{122}$, $R^{131}$, $R^{132}$, $R^{141}$ and $R^{142}$ are preferably the same.

$R^{103}$, $R^{113}$, $R^{123}$, $R^{133}$ and $R^{143}$ are preferably a halogen atom, an alkyl group, an alkenyl group, an alkinyl group, an aryl group, a cyano group, a hydroxyl group, a carboxyl group, an alkoxy group, an aryloxy group, a silyloxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an imide group, a phosphino group, a phosphinyl group, a phosphinyloxy group, a phosphinylamino group or a silyl group, more preferably a halogen atom, an alkyl group, an alkenyl group, an aryl group, a cyano group, a hydroxyl group, a carboxyl group, an alkoxy group, an aryloxy group, a silyloxy group, an amino group, an alkylthio group, an arylthio group, an imide group or a silyl group, still more preferably a halogen atom, an alkyl group, an aryl group, an alkoxy group, an aryloxy group, a silyloxy group and an amino group or most preferably an alkyl group. Also, all of $R^{113}$, $R^{123}$, $R^{133}$ and $R^{143}$ are preferably the same.

$n_{103}$, $n_{113}$, $n_{123}$, $n_{133}$ and $n_{143}$ are preferably 0 to 3, more preferably 0 to 2, still more preferably 0 or 1 and most preferably 0.

In the formula (II) $R^{211}$, $R^{212}$, $R^{221}$, $R^{222}$, $R^{231}$, $R^{232}$, $R^{241}$ and $R^{242}$ respectively have the same meaning as above $R^{111}$ and the preferable range is also the same. Also, all of $R^{211}$, $R^{212}$, $R^{221}$, $R^{222}$, $R^{231}$, $R^{232}$, $R^{241}$ and $R^{242}$ are preferably the same.

$R^{203}$, $R^{213}$, $R^{223}$, $R^{233}$ and $R^{243}$ respectively have the same meaning as above $R^{103}$ and the preferable range is also the same. Also, all of $R^{213}$, $R^{223}$, $R^{233}$ and $R^{243}$ are preferably the same.

$n_{203}$, $n_{213}$, $n_{223}$, $n_{233}$ and $n_{243}$ respectively have the same meaning as above $n_{103}$ and the preferable range is also the same.

X represents a monovalent or divalent anion. X is preferably a perchloric acid ion, a carboxylic acid ion, a sulfonic acid ion, a hexafluorophosphoric acid ion, a tetrafluoroboric acid ion or a hexafluoroantimonic acid ion, more preferably a perchloric acid ion, a sulfonic acid ion, a hexafluorophosphoric acid ion, a tetrafluoroboric acid ion or a hexafluoroantimonic acid ion, still more preferably a perchloric acid ion, a hexafluorophosphoric acid ion, a tetrafluoroboric acid ion or a hexafluoroantimonic acid ion, and most preferably a perchloric acid ion.

Specific examples of the compounds represented by the formulae (I) and (II) will be shown below: however, these examples are not intended to be limiting of the present invention.

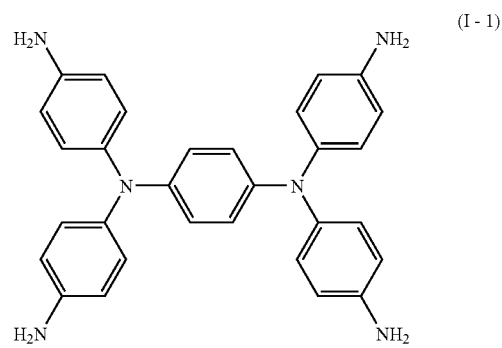

(I-1)

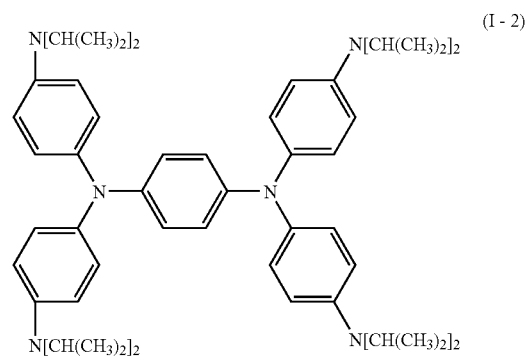

(I-2)

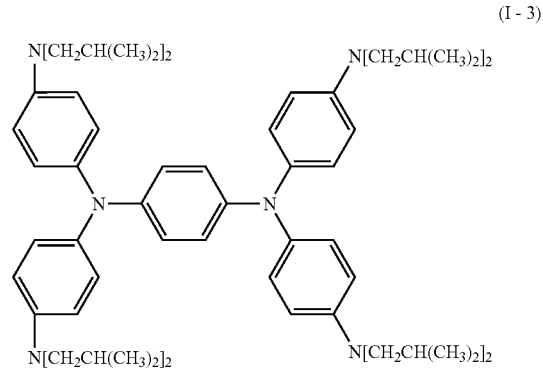

(I-3)

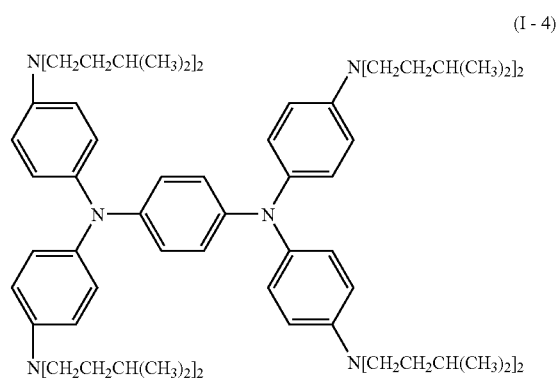

(I-4)

-continued
(I-5)
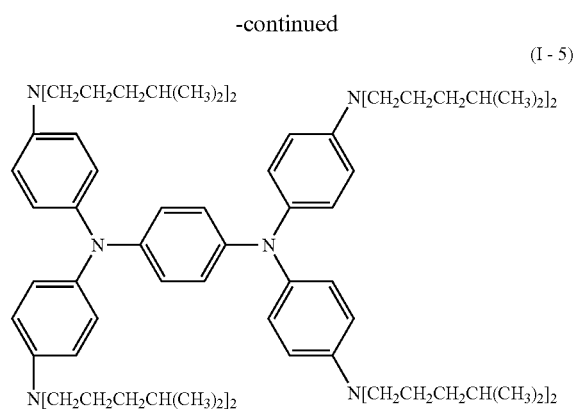
(I-9)
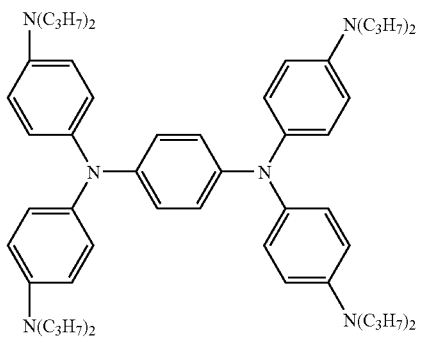
(I-6)
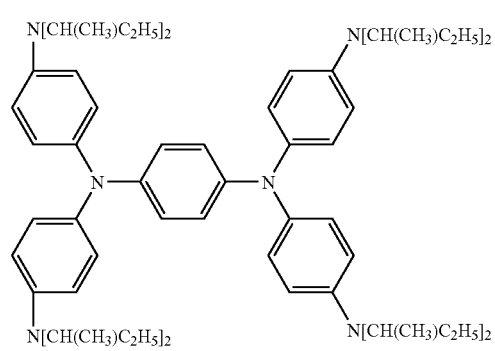
(I-10)
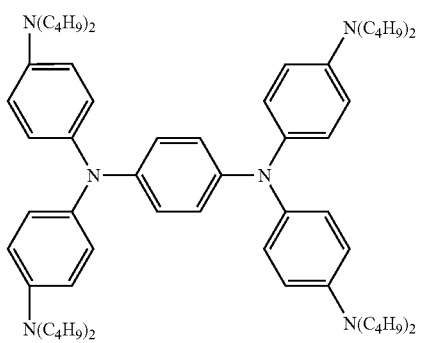
(I-7)
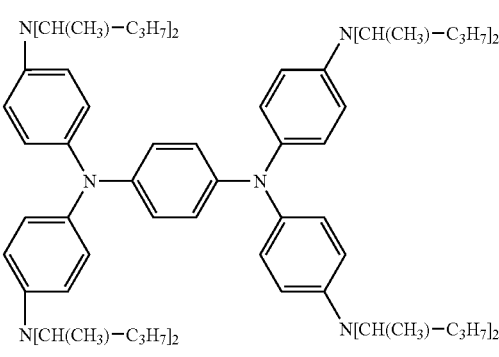
(I-11)
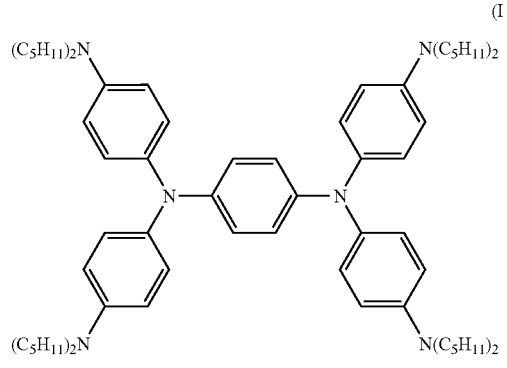
(I-8)
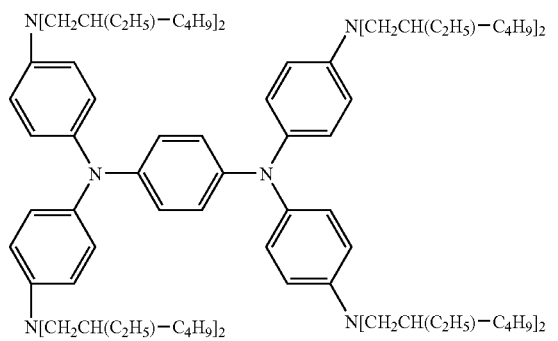
(I-12)
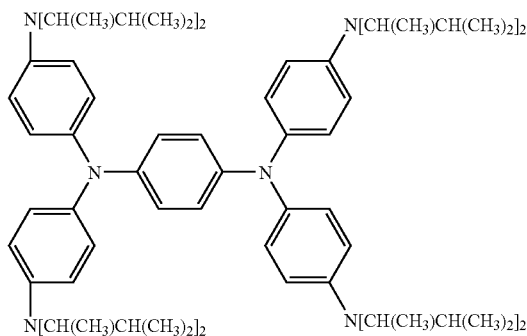

(I-13)
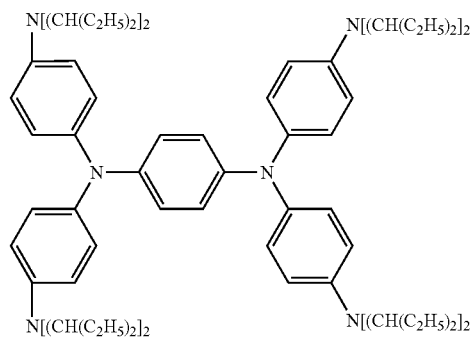
(I-14)
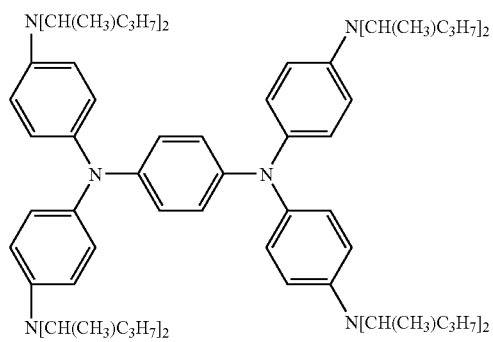
(I-15)
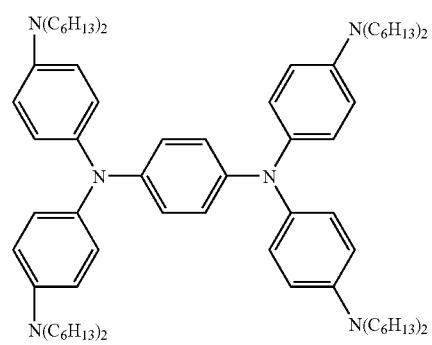
(I-16)
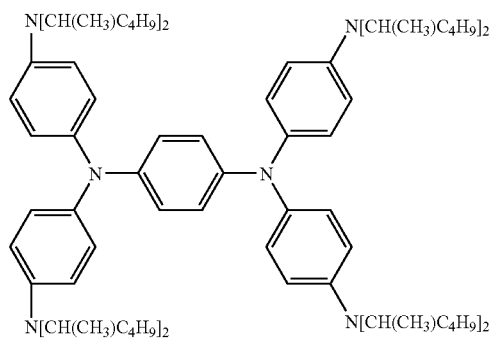
(I-17)
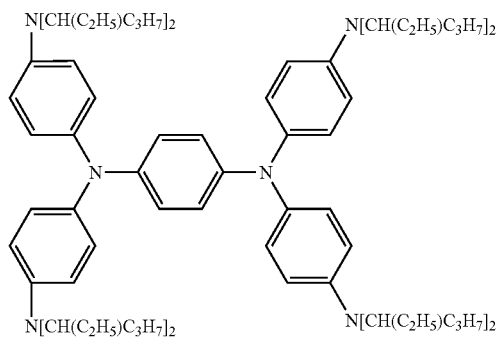
(I-18)
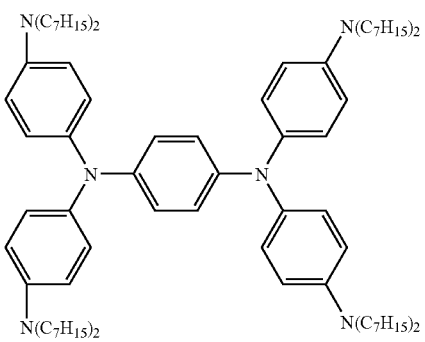
(I-19)
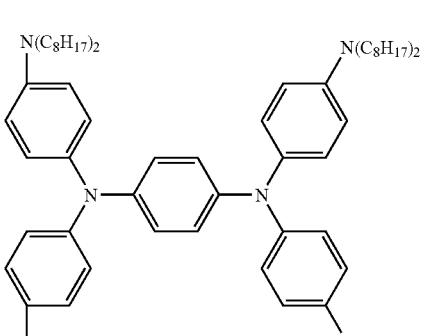
(I-20)
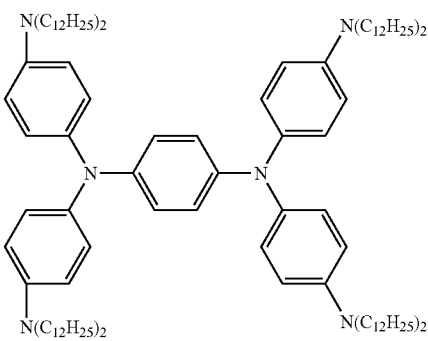

-continued

-continued
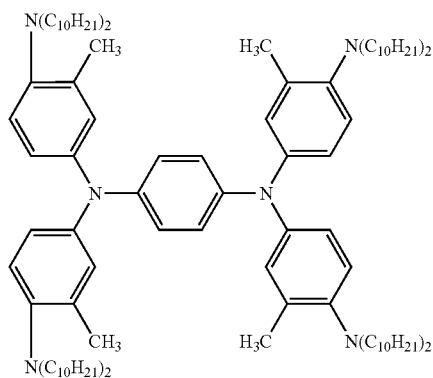
(I - 29)
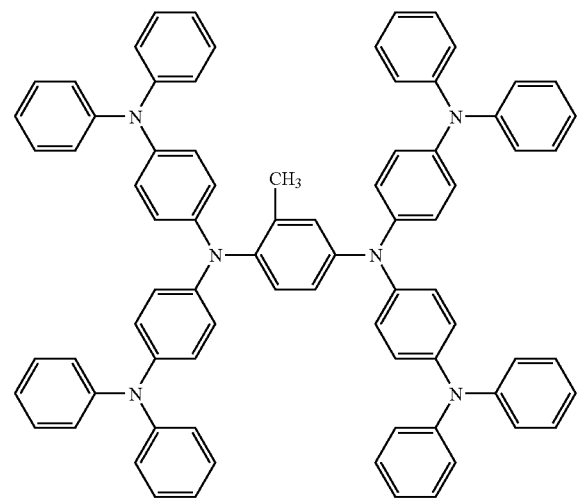
(I - 30)
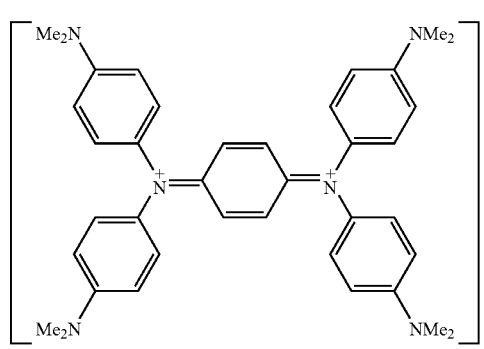
(II - 1)
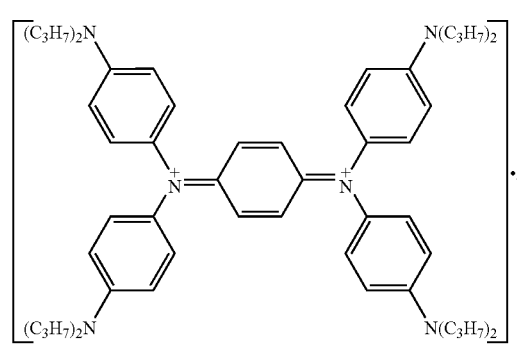
(II - 2)
-continued
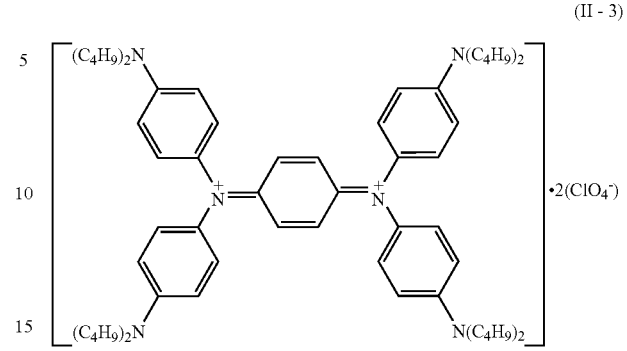
(II - 3)
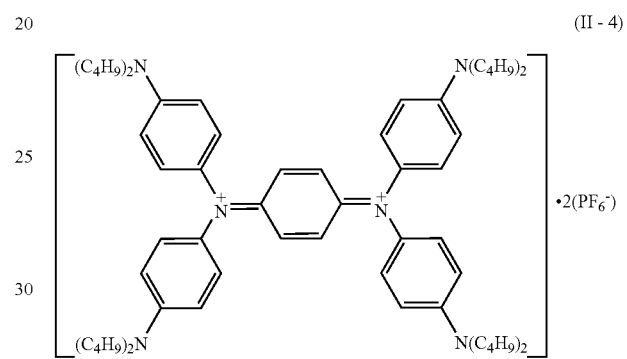
(II - 4)
(II - 5)
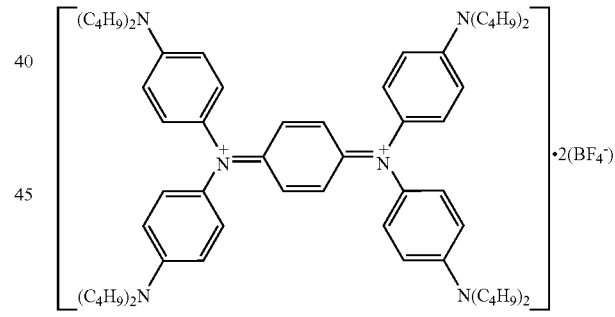
(II - 6)

-continued
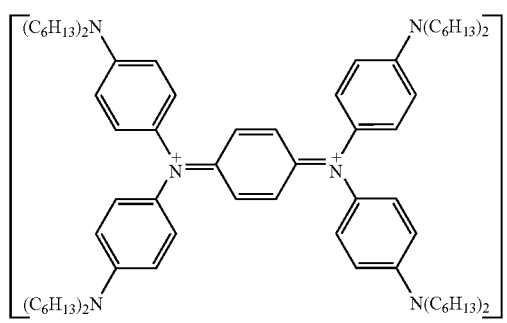
(II-7)
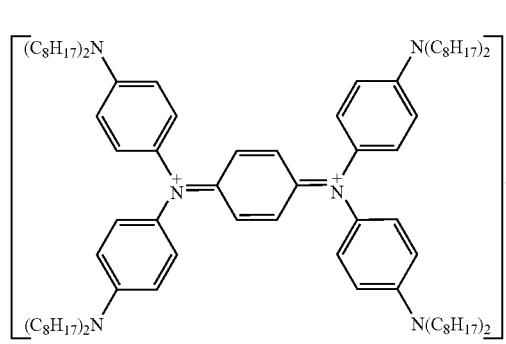
(II-8)
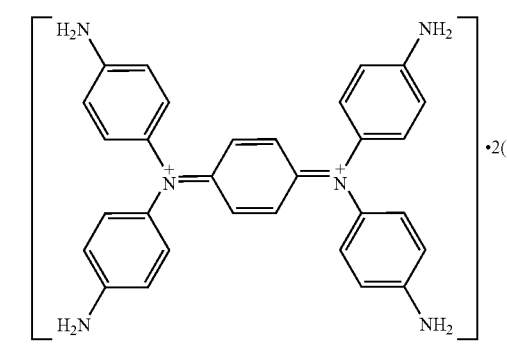
(II-9)
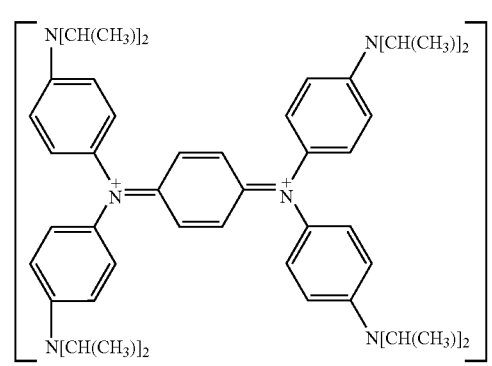
(II-10)
-continued
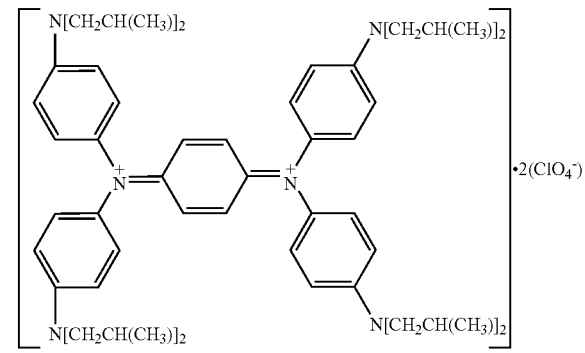
(II-11)
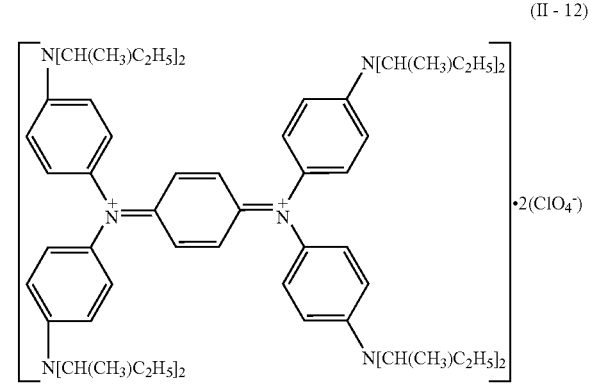
(II-12)
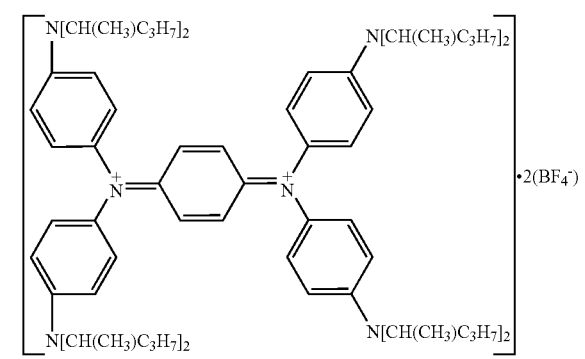
(II-13)
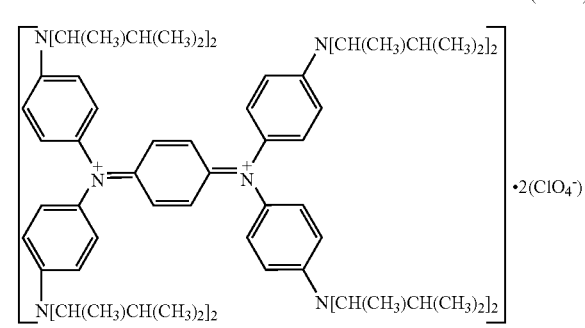
(II-14)

-continued
(II-15)
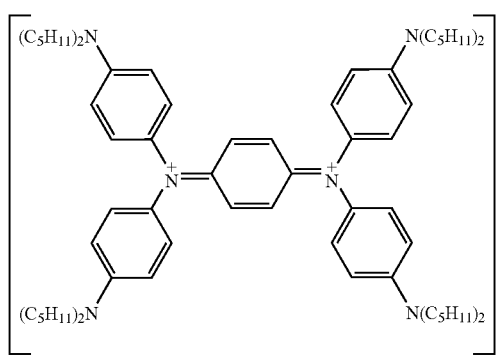
(II-19)
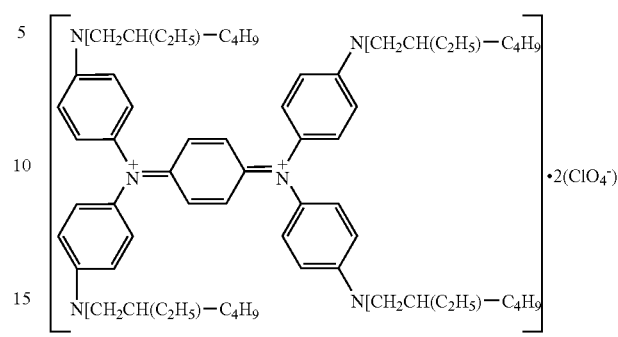
(II-16)
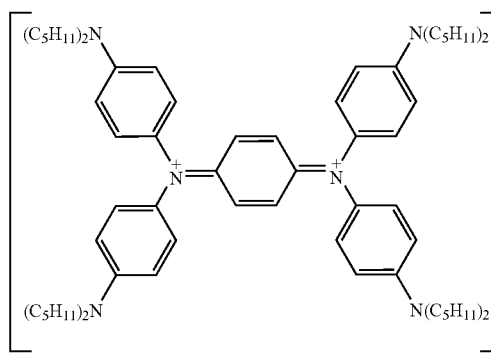
(II-20)
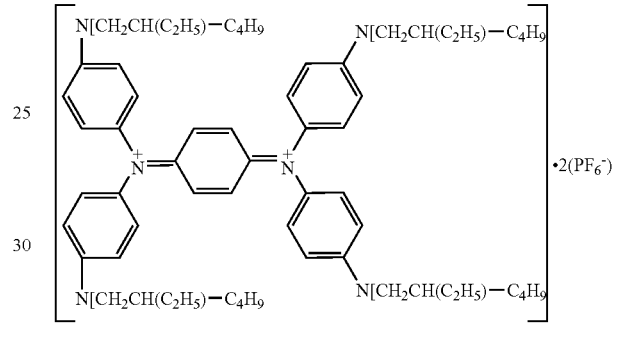
(II-17)
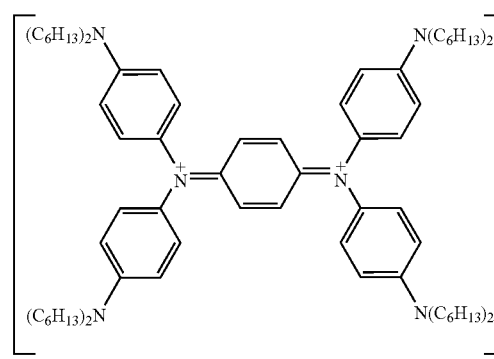
(II-21)
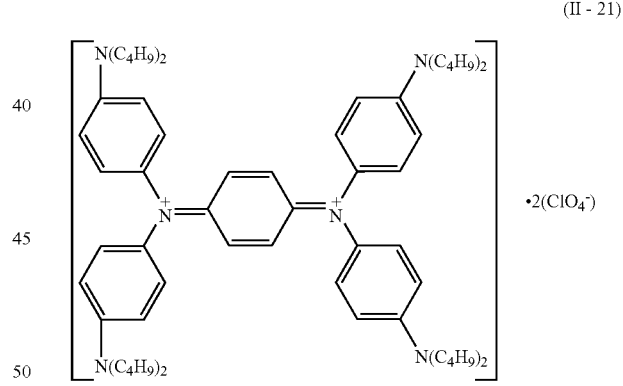
(II-18)
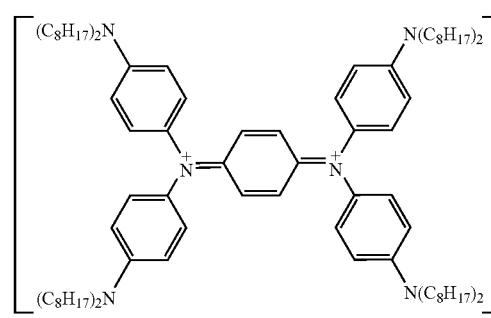
(II-22)
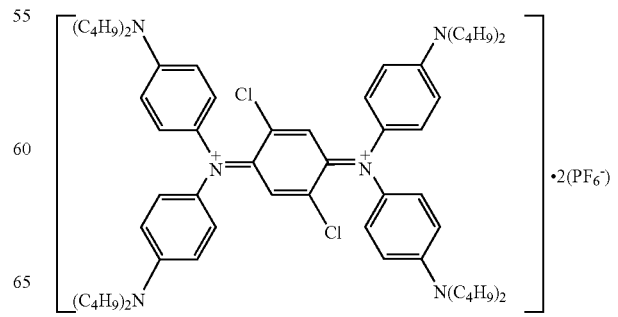

-continued
(II-23)
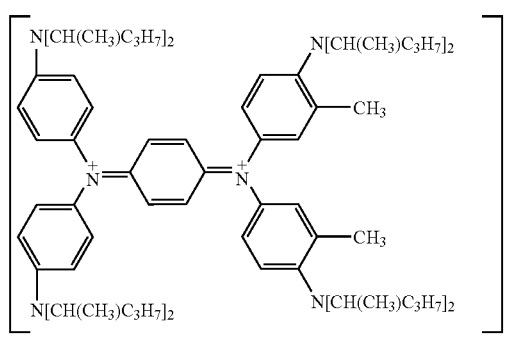
(II-24)
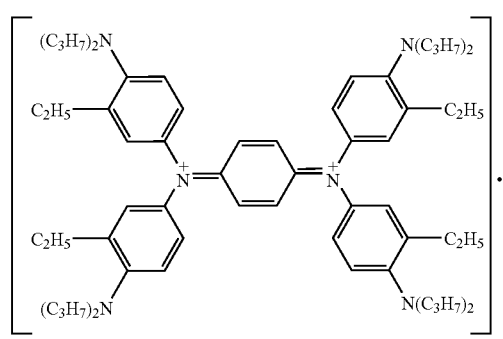
(II-25)
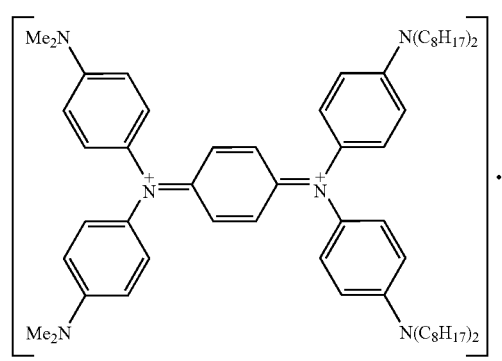
(II-26)
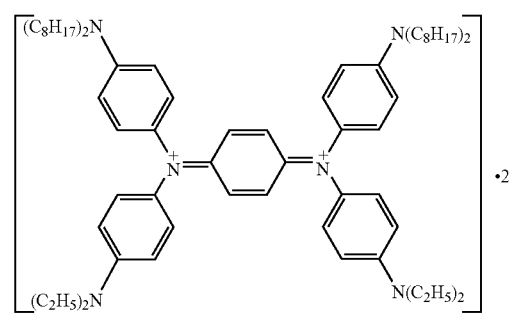
-continued
(II-27)
(II-28)
(II-29)
(II-30)
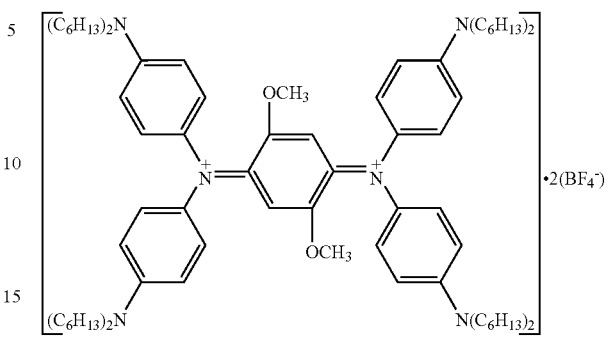

As the halogenating agent to be used in the present invention, inorganic or organic halogenating agents are given. These agents may be used either singly or in combinations of two or more. Preferable examples of the inorganic halogenating agent include halogen molecules (for example, fluorine, chlorine, bromine and iodine), sulfur compounds (for example, sulfuryl chloride and sulfuryl bromide), phosphorous compounds (for example, phosphorous trichloride, phosphorous pentachloride, phosphorous tribromide and phosphorous pentabromide) and halogen oxide ions (for example, sodium chlorate). Examples of the organic halogenating agents include N-halides (for example, trichloroisocyanuric acid, 1,3-dichloro-5,5-dimethylhydantoin, 1,3-dibromo-5,5-dimethylhydantoin, N-chlorosuccinic acid imide and N-bromosuccinic acid imide) and compounds in which the α-position of the carbonyl is halogenated (for example, dichloromerdramic acid, dibromomerdramic acid and hexachloroacetone). Among these compounds, sulfuryl chloride, phosphorous pentachloride, trichloroisocyanuric acid, 1,3-dichloro-5,5-dimethylhydantoin, 1,3-dibromo-5,5-dimethylhydantoin, N-chlorosuccinic acid imide and N-bromosuccinic acid imide are preferable. More preferable compounds are chlorinating agents in organic halogenating agents, for example trichloroisocyanuric acid, 1,3-dichloro-5,5-dimethylhydantoin and N-chlorosuccinic acid imide, and most preferable compound is 1,3-dichloro-5,5-dimethylhydantoin.

It is preferable that an acid or its salt coexist in the oxidizing process of the present invention.

Examples of such an acid (protonic body) or its salt include acids such as perchloric acid, benzoic acid, hexafluorophosphoric acid, tetrafluoroboric acid, p-toluenesulfonic acid, methanesulfonic acid, ethanesulfonic acid, benzenesulfonic acid, naphthalene-1,5-disulfonic acid, trifluoroacetic acid, hexafluoroantimonic acid, trifluoromethanesulfonic acid and molybudenic acid or its ammonium salts, lithium salts, sodium salts, potassium salts and magnesium salts of these acids. Among these compounds, protonic bodies of a perchloric acid, hexafluorophosphoric acid, tetrafluoroboric acid, methanesulfonic acid, hexafluoroantimonic acid or trifluorometanesulfonic acid, ammonium salts, sodium salts or potassium salts of these protonic bodies, more preferably protonic bodies of a perchloric acid, hexafluorophosphoric acid, tetrafluoroboric acid or hexafluoroantimonic acid, sodium salts or potassium salts of these protonic bodies, and most preferably protonic bodies of a perchloric acid, sodium hydrogenperchlorate or potassium perchlorate.

As to the ratio of raw materials used, a halogenatiiong agent is used in a ratio by mol of, preferably, 0.1 to 10 mol, more preferably 0.2 to 5 mol, still more preferably 0.5 to 4 mol and still more preferably 0.6 to 3 mol to one mol of the compound represented by the formula (I).

The acid or its salt is used in a ratio by mol of, preferably, 0.5 to 20 mol, more preferably 1 to 10 mol, still more preferably 1.5 to 5 mol and still more preferably 2 to 4 mol to one mol of the compound represented by the formula (I).

As the solvent used in the reaction, for example, water, an amide type solvent (for example, N,N-dimethylformamide, N,N-dimethylacetamide and 1-methyl-2-pyrrolidone), sulfonic type solvent (for example, sulfolane), sulfoxide type solvent (for example, dimethylsulfoxide), ureide type solvent (for example, tetramethylurea), ether type solvent (for example, dioxane and cyclopentyl methyl ether), ketone type solvent (for example, acetone and cyclohexanone), hydrocarbon type solvent (for example, toluene, xylene and n-decane), halogen type solvent (for example, tetrachloroethane and chlorobenzene), alcohol type solvent (for example, methanol, ethanol, isopropyl alcohol, ethylene glycol, cyclohexanol and phenol), pyridine type solvent (for example, pyridine, γ-picoline and 2,6-lutidine), ester type solvent (for example, ethyl acetate and butyl acetate), carboxylic acid type solvent (for example, acetic acid and propionic acid) and nitrile type solvent (for example, acetonitrile) may be used either singly or in combinations. Among these compounds, water, an amide type solvent, sulfone type solvent, sulfoxide type solvent, ureide type solvent, halogen type solvent, alcohol type solvent, pyridine type solvent, ester type solvent, carboxylic acid type solvent and nitrile type solvent are preferable, water, an amide type solvent, sulfone type solvent, ureide type solvent, halogen type solvent, alcohol type solvent, ester type solvent and nitrile type solvent are more preferable, and water, sulfone type solvent, alcohol type solvent, ester type solvent and nitrile type solvent are still more preferable. Also, it is preferable to use a combination of water and other solvents.

The reaction temperature is −30 to 250° C., preferably −10 to 150° C., still more preferably −5 to 110° C., even more preferably 0 to 70° C. and even more preferably 10 to 50° C. It is also preferable to run the reaction at −5 to 20° C. at the start of the reaction and then at the temperature raised to 25 to 100° C. from the middle of the reaction.

According to the present invention, it is possible to provide a method in which an aminium salt and a diimmonium salt, which are near-infrared absorption dye compounds which are useful for image forming materials, infrared heat-sensitive recording materials, optical recording devices and optical film materials, can be produced readily, at low costs and in high yield.

The present invention will be described in more detail based on the following examples, but the present invention is not limited thereto.

EXAMPLES

Example 1

Synthesis of the Exemplified Compound (II-3)

The exemplified compound (II-3) was synthesized according to the following scheme.

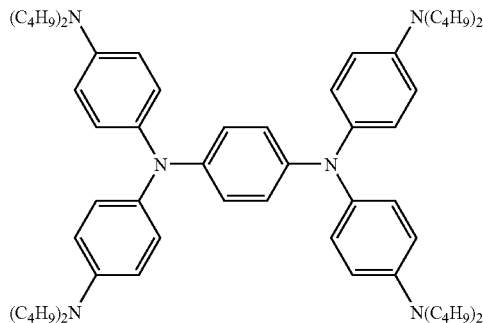
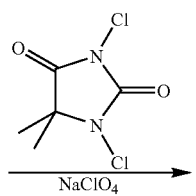

(Exemplified compound (I-10))

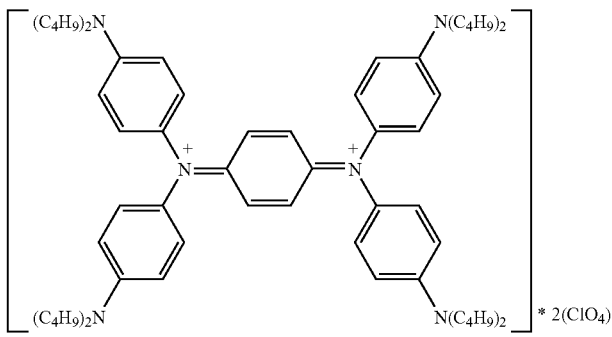

(Exemplified compound (II-3))

In a three-neck flask, 9.21 g of the exemplified (I-10) was dissolved in 120 ml of ethyl acetate and the mixture was stirred at ambient temperature. An aqueous solution prepared by dissolving 2.44 g of sodium perchlorate in 40 ml of water was added dropwise to the mixture over 5 minutes, 2.37 g of 1,3-dichloro-5,5-dimethylhydantoin was added to the mixture over for 5 minutes, which was then stirred for 1 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 9.74 g of the exemplified compound (II-3) (yield: 87%). The mass-spectrum of these crystals were measured in a unionized state to obtain the following results m/z=460. Also, DSC of these crystals was measured to obtain the following results: exothermic starting temperature: 186° C. and calorific value: 1,420 J/g.

Example 2

Synthesis of the Exemplified Compound (II-3)

The exemplified compound (II-3) was synthesized according to the following scheme.

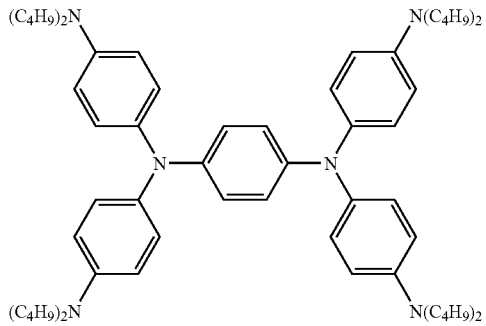
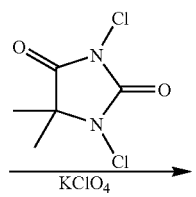

(Exemplified compound (I-10))

-continued

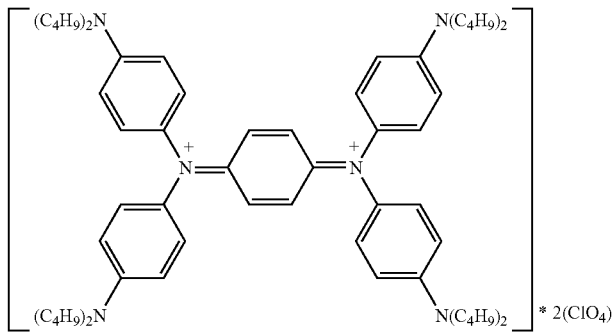

(Exemplified compound (II-3))

In a three-neck flask, 9.21 g of the exemplified (I-10) was dissolved in 120 ml of ethyl acetate and the mixture was stirred at ambient temperature. An aqueous solution prepared by dissolving 2.77 g of potassium perchlorate in 40 ml of water was added dropwise to the mixture over 5 minutes, 2.37 g of 1,3-dichloro-5,5-dimethylhydantoin was added to the mixture over for 5 minutes, which was then stirred for 1 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 9.41 g of the exemplified compound (II-3) (yield: 84%). The mass-spectrum of these crystals were measured in a unionized state to obtain the following results m/z=460.

Example 3

Synthesis of the
Exemplified Compound (II-15)

The exemplified compound (II-15) was synthesized according to the following scheme.

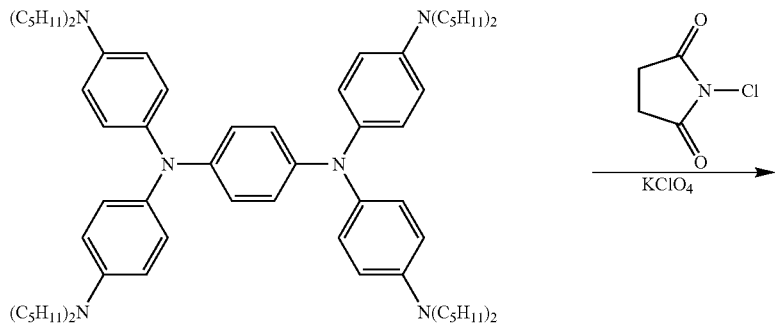

(Exemplified compound (I-11))

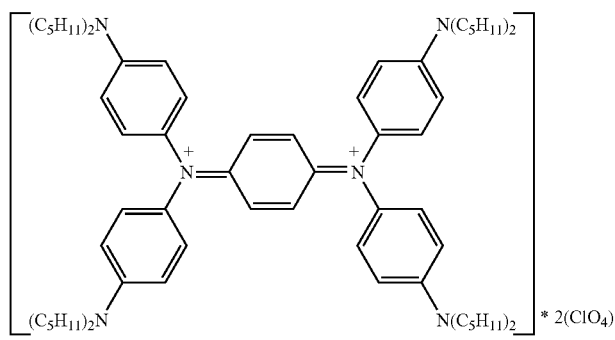

(Exemplified compound (II-15))

In a three-neck flask, 10.3 g of the exemplified (I-11) was dissolved in 160 ml of ethyl acetate and the mixture was stirred at ambient temperature. An aqueous solution prepared by dissolving 2.77 g of potassium perchlorate in 40 ml of water was added dropwise to the mixture over 5 minutes, 3.34 g of N-chlorosuccinic acid imide was added to the mixture over for 5 minutes, which was then stirred for 3 hours as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 9.85 g of the exemplified compound (II-15) (yield: 80%). The mass-spectrum of these crystals were measured in a unionized state to obtain the following results m/z=516.

Example 4

Synthesis of the
Exemplified Compound (II-7)

The exemplified compound (II-7) was synthesized according to the following scheme.

In a three-neck flask, 11.46 g of the exemplified (I-15) was dissolved in 200 ml of ethyl acetate and the mixture was stirred at ambient temperature. In this mixture, 4.00 g of 1,3-dibromo-5,5-dimethylhydantoin was added over for 10 minutes, which was then stirred for 2 hours as it was. An aqueous solution dissolving 2.77 g of potassium perchlorate in 40 ml of water was added, and the mixture was stirred for 1 hour as it was. The resulting solution was fractionated and washed with a mixture solution of 60 ml of water and 10 ml of saturated brine three times. Then, the resulting mixture was concentrated by a rotary evaporator, ethyl acetate was added to the obtained residue and the obtained crystals were subjected to filtration and drying to obtain 9.96 g of the exemplified compound (II-7) (yield: 74%). The mass-spectrum of these crystals were measured in a unionized state to obtain the following results m/z=572.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing a near-infrared absorbing dye compound, comprising a process of reacting a compound represented by formula (I) with a halogenating agent:

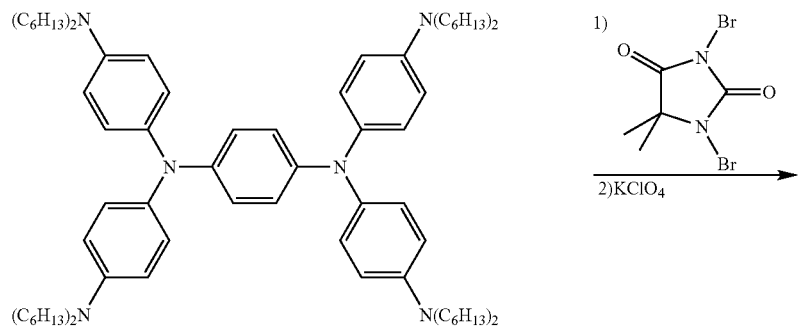

(Exemplified compound ( I - 15 ))

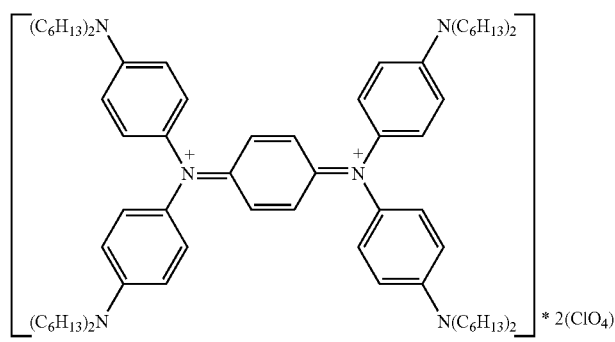

(Exemplified compound ( II - 7 ))

Formula (I)

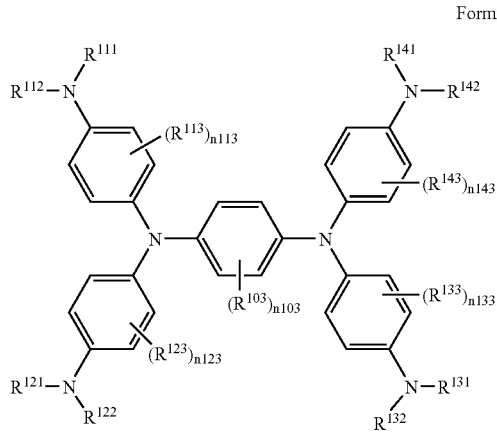

wherein $R^{111}$, $R^{112}$, $R^{121}$, $R^{122}$, $R^{131}$, $R^{132}$, $R^{141}$ and $R^{142}$ each independently represent a hydrogen atom, an aliphatic group or an aromatic group; $R^{103}$, $R^{113}$, $R^{123}$, $R^{133}$ and $R^{143}$ each independently represent a substituent; and $n_{103}$, $n_{113}$, $n_{123}$, $n_{133}$ and $n_{143}$ each independently denote an integer from 0 to 4.

2. The production method according to claim 1, wherein the halogenating agent is an organic halogenating agent.

3. The production method according to claim 1, wherein the halogenating agent is a chlorinating agent.

4. The production method according to claim 1, wherein the halogenating agent is 1,3-dichloro-5,5-dimethylehydantoin.

5. The production method according to claim 1, wherein the near-infrared absorbing dye compound is a diimmonium salt represented by formula (II):

Formula (II)

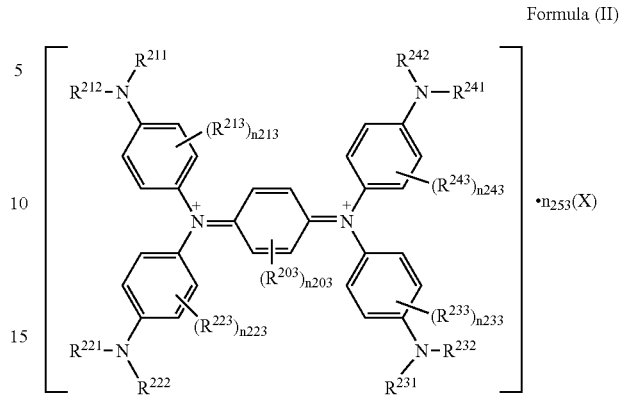

wherein $R^{211}$, $R^{212}$, $R^{221}$, $R^{222}$, $R^{231}$, $R^{232}$, $R^{241}$ and $R^{242}$ each independently represent a hydrogen atom, an aliphatic group or an aromatic group; $R^{203}$, $R^{213}$, $R^{223}$, $R^{233}$ and $R^{243}$ each independently represent a substituent; $n_{203}$, $n_{213}$, $n_{223}$, $n_{233}$ and $n_{243}$ each independently denote an integer from 0 to 4; X represents a monovalent or divalent anion; and $n_{253}$ represents a number of 1 or 2, provided that the product of the valence number of X and $n_{253}$ is 2.

6. The production method according to claim 1, wherein an acid or its salt coexists in the above process.

7. The production method according to claim 6, wherein the above acid or salt is perchloric acid or perchlorate.

\* \* \* \* \*